United States Patent
Barrelle

(10) Patent No.: US 7,390,312 B2
(45) Date of Patent: Jun. 24, 2008

(54) PASSIVE SAFETY SHIELD SYSTEM FOR INJECTION DEVICES

(75) Inventor: Laurent Barrelle, Saint Nizier du Moucherotte (FR)

(73) Assignee: Becton, Dickinson and Company, Franklin Lakes, NJ (US)

(*) Notice: Subject to any disclaimer, the term of this patent is extended or adjusted under 35 U.S.C. 154(b) by 741 days.

(21) Appl. No.: 10/896,346

(22) Filed: Jul. 21, 2004

(65) Prior Publication Data
US 2005/0004552 A1    Jan. 6, 2005

Related U.S. Application Data

(62) Division of application No. 10/143,414, filed on May 10, 2002, now Pat. No. 6,776,777.

(51) Int. Cl.
*A61M 5/32* (2006.01)
*A61M 5/00* (2006.01)

(52) U.S. Cl. .................................. 604/110; 604/198
(58) Field of Classification Search ................ 604/110, 604/192–198, 181, 187, 263, 163; 128/919
See application file for complete search history.

(56) References Cited

U.S. PATENT DOCUMENTS 6,966,898 B1   11/2005  Pouget et al.

2002/0120239 A1    8/2002  Jansen et al.
2002/0156426 A1   10/2002  Gagnieux et al.
2002/0193746 A1*  12/2002  Chevallier .................... 604/197
2003/0050607 A1*   3/2003  Gagnieux et al. ........... 604/198
2003/0212380 A1   11/2003  Barelle
2005/0004528 A1    1/2005  Barrelle et al.
2005/0148943 A1    7/2005  Chevalier
2006/0036216 A1    2/2006  Rimlinger et al.

FOREIGN PATENT DOCUMENTS

| EP | 0966983 | 12/1999 |
|---|---|---|
| FR | 2799976 | 4/2001 |
| FR | 2821561 | 9/2002 |
| FR | 2830765 | 4/2003 |
| FR | 2835753 | 8/2003 |
| WO | WO 02/070054 | 9/2000 |
| WO | WO 01/41841 | 6/2001 |

* cited by examiner

*Primary Examiner*—Matthew F Desanto
(74) *Attorney, Agent, or Firm*—David M. Fortunato; Cohen Pontani Lieberman Pavane LLP

(57) ABSTRACT

A passive shield system for a syringe including a body, shield, spring and ring which provide an interlock of the shield in the retracted position prior to receipt of the syringe for bulk transportation and processing and wherein the user selects the timing of the release of the shield to its extended position following injection, but which assures shielding of the syringe needle following release of the syringe plunger.

7 Claims, 14 Drawing Sheets

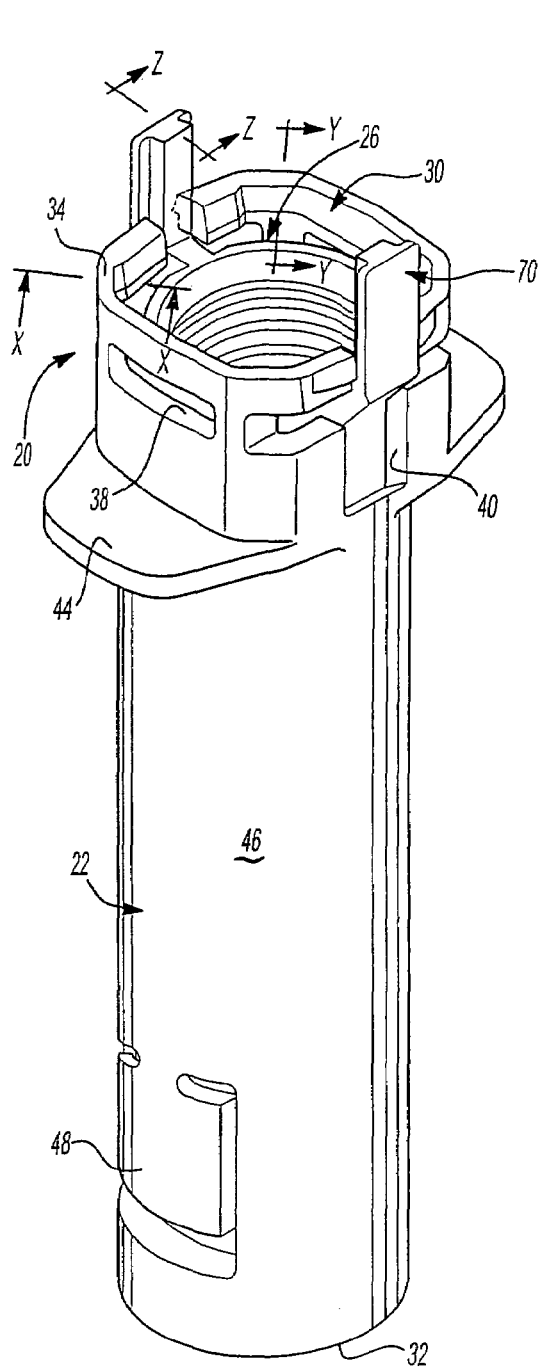
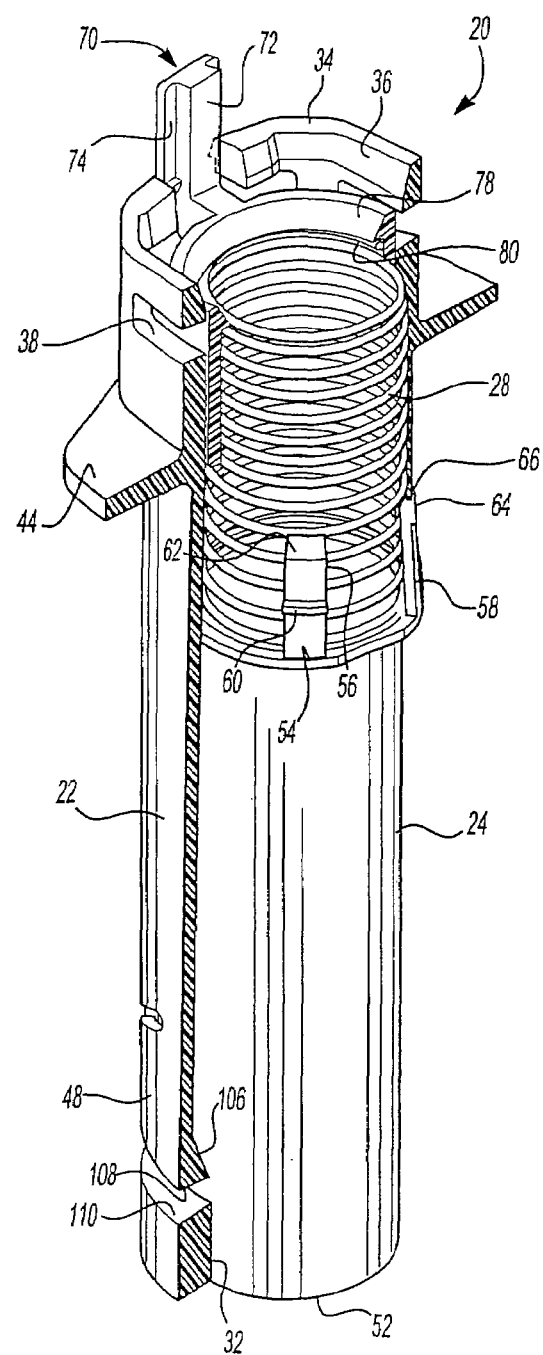
Fig-1
Fig-2

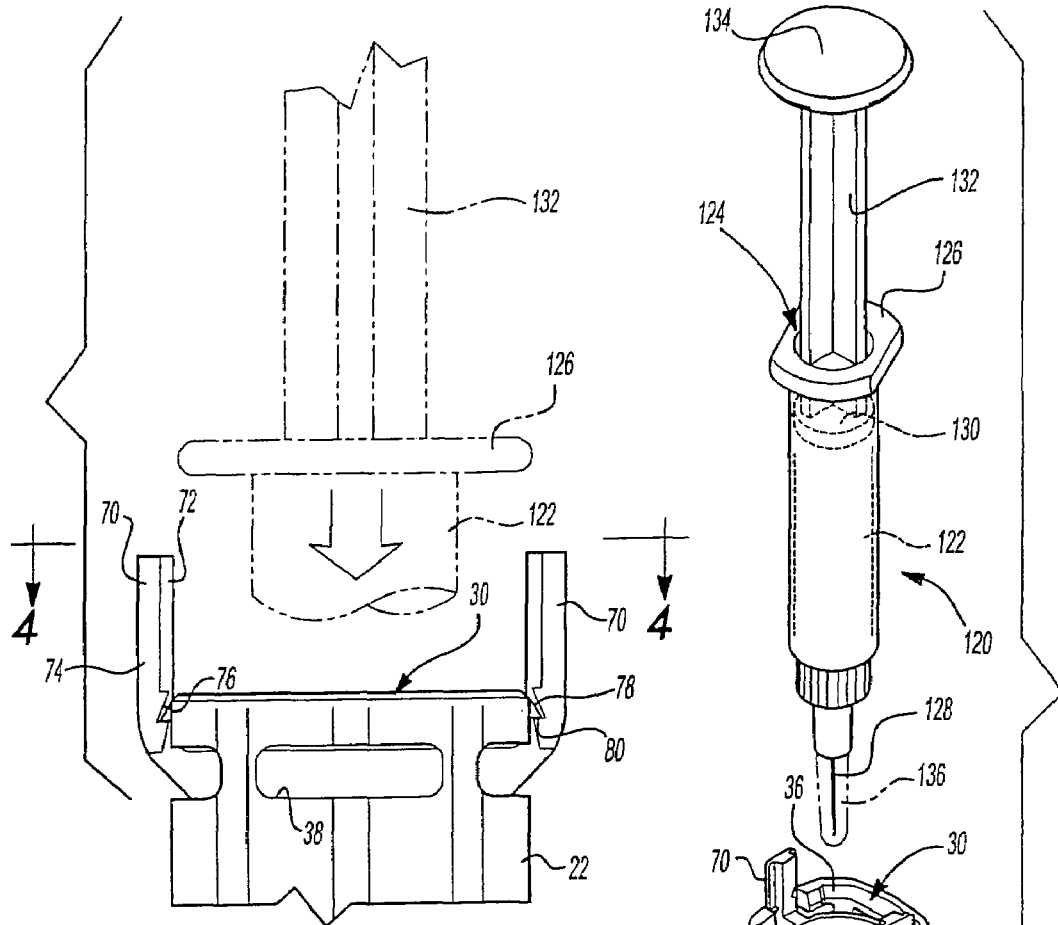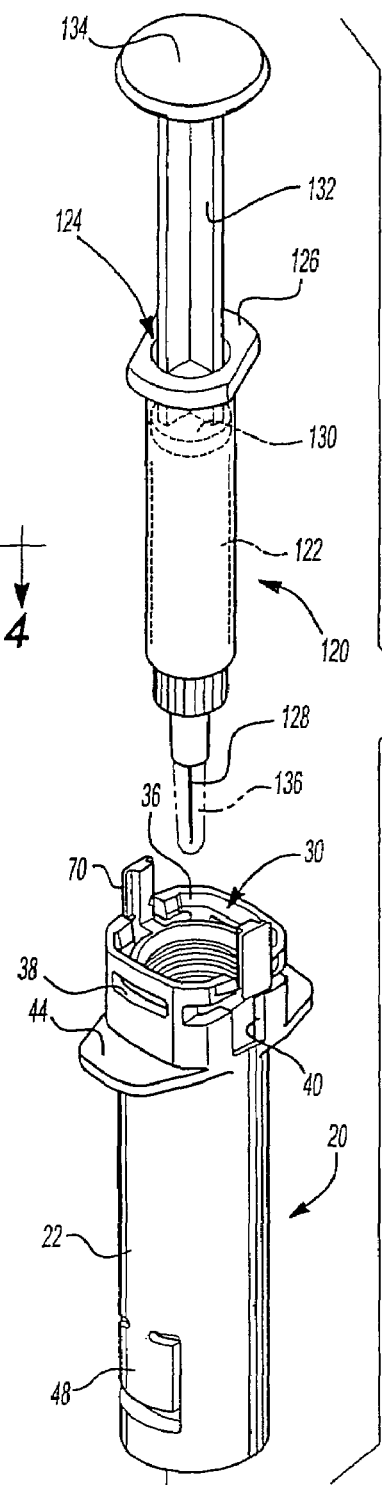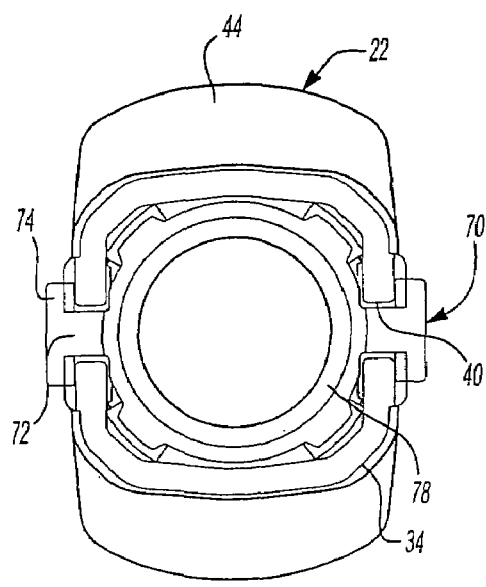

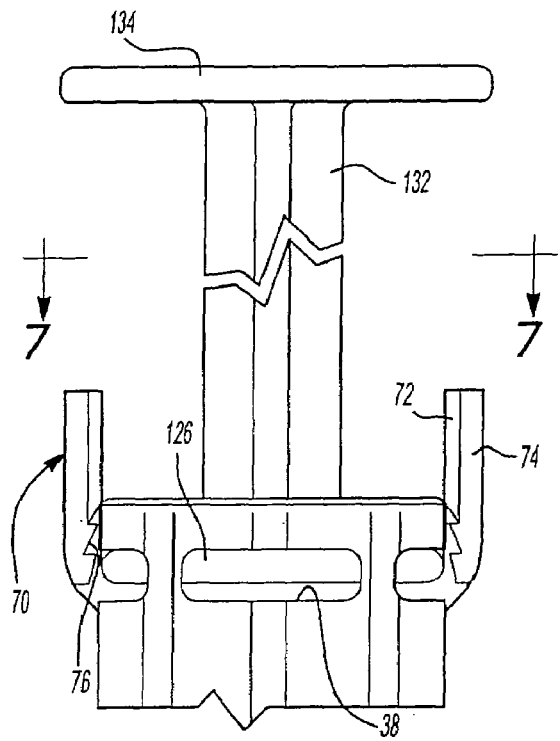
Fig-6
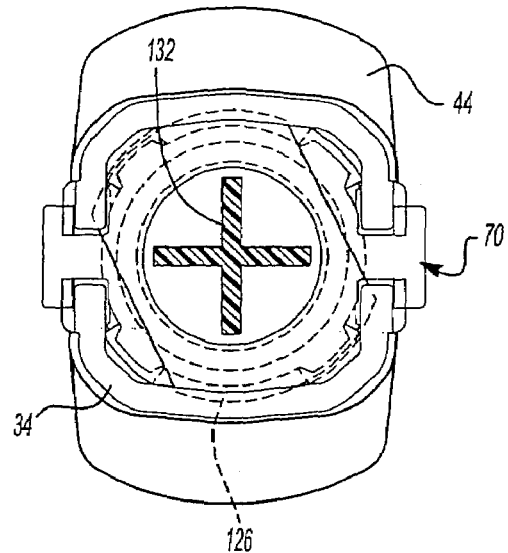
Fig-7
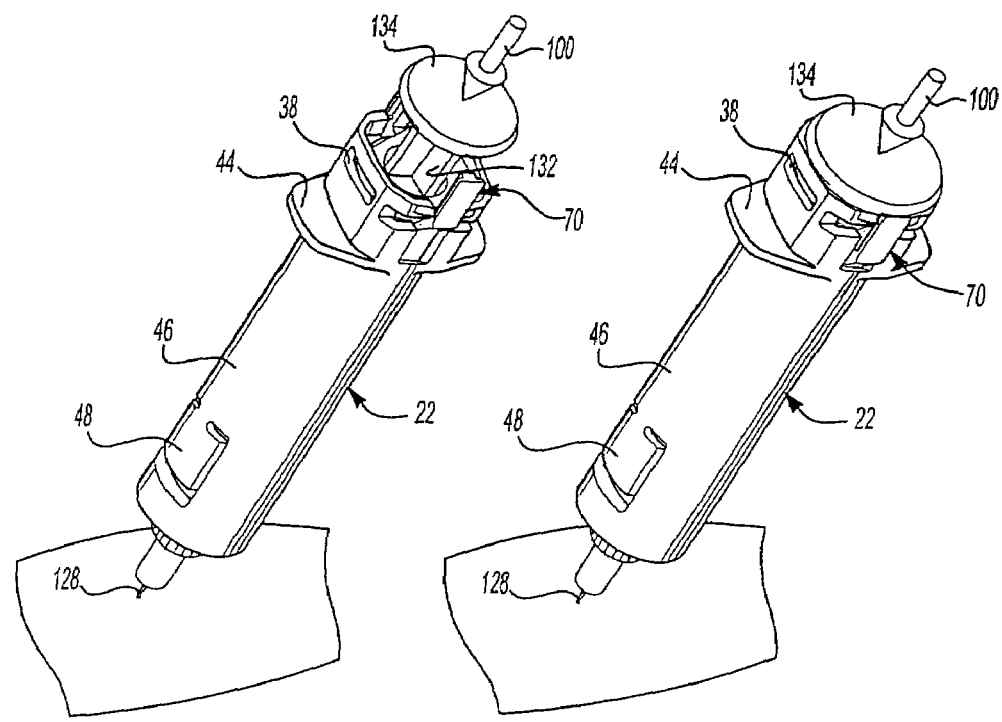
Fig-8
Fig-9

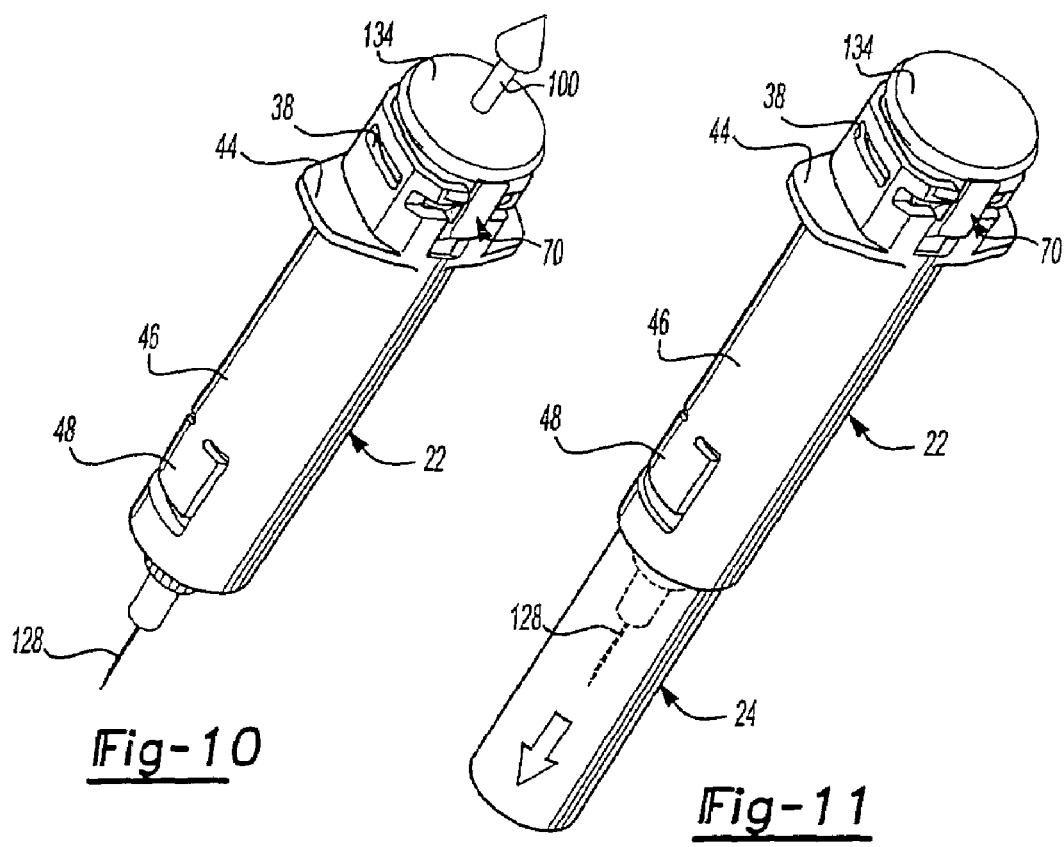

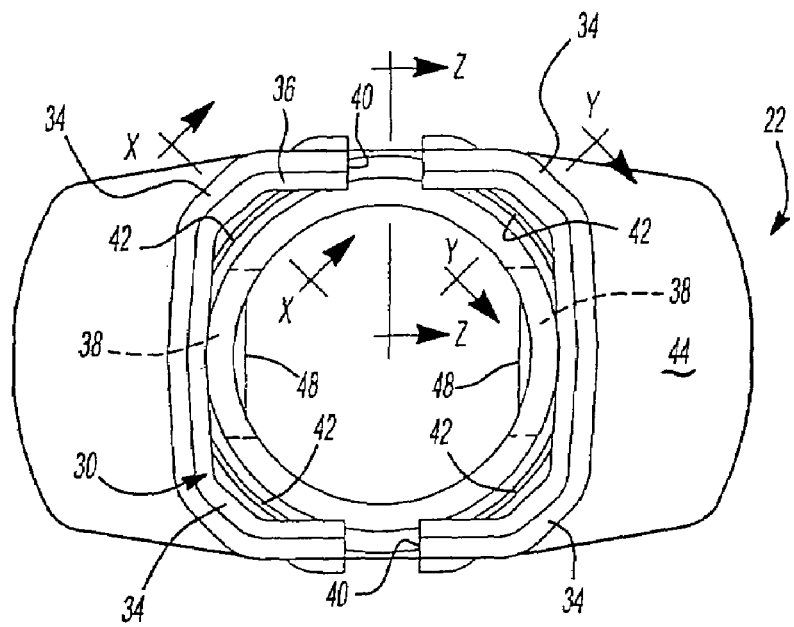

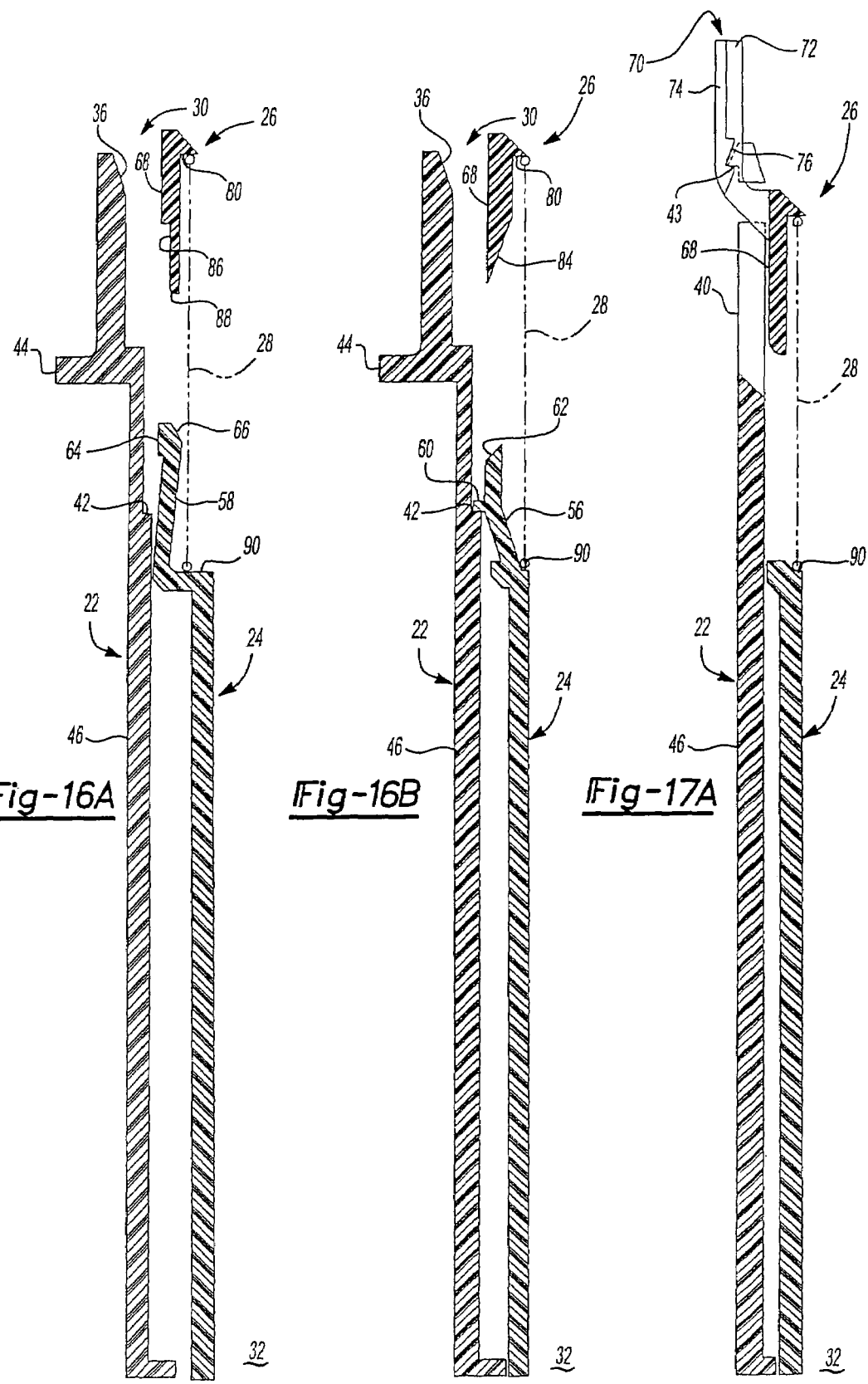

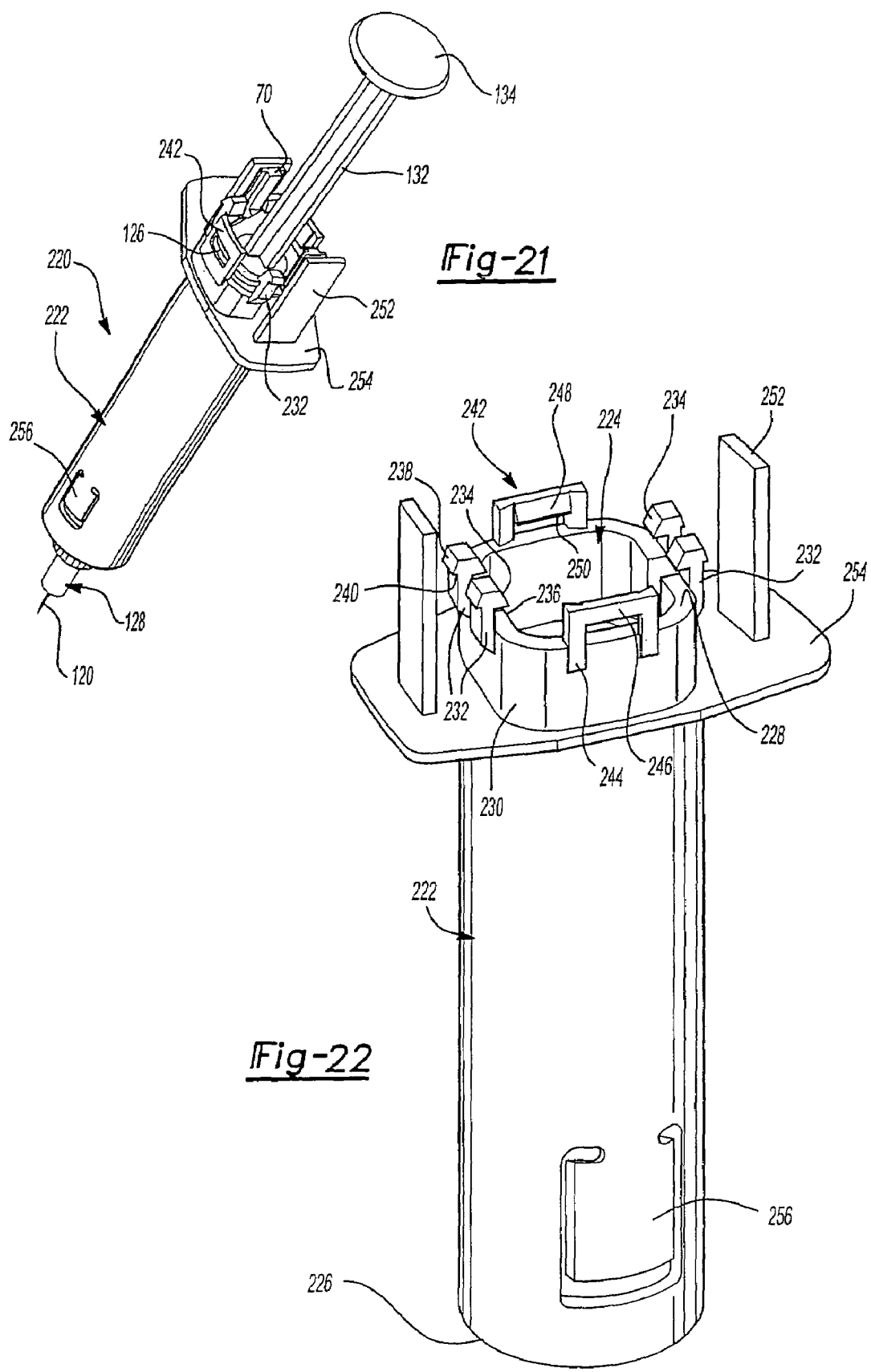

ered position, wherein the needle is exposed for injection or aspiration in the case of reconstitution or vein test, to the extended position, wherein the needle is enclosed. Such manual shield systems typically include some means to prevent the shield from being inadvertently moved to the extended position and prevent the shield from retracting following shielding of the syringe needle cannula, such as detents, interlocking ribs, threads, spiral grooves and the like. The principal disadvantages of manual syringe shield systems are that there is no positive assurance that the user will properly shield the needle cannula following use or that the needle cover is properly locked in the shielded position. In addition, some designs can allow inadvertent activation of the shield.

PASSIVE SAFETY SHIELD SYSTEM FOR INJECTION DEVICES

This is a divisional of U.S. application Ser. No. 10/143,414, filed May 10, 2002 now U.S. Pat. No. 6,776,777.

FIELD OF THE INVENTION

The present invention relates to a passive shield system for injection devices, including syringes, which prevents inadvertent or premature actuation of the shield during normal bulk transportation, handling and processing and permits the user, such as a healthcare worker or patient, to select the timing of the actuation of the shield while assuring shielding of the needle or cannula without additional manual manipulation.

BACKGROUND OF THE INVENTION

Injection devices including syringes are well known medical devices for administering medicaments, drugs and vaccines to patients. As used herein, the term "syringe" is intended to cover the various types of injection and medical delivery devices. They are also used for other well known purposes in the medical field. Prefilled syringes, for example, are generally considered as those which are filled with a selected dosage of medicament, drug or vaccine by a pharmaceutical manufacturer for distribution to the end user. They are generally comprised of a tubular barrel, which contains the medicament, drug or vaccine and a stopper is slidably received in the barrel. The distal end of the barrel typically includes a needle cannula affixed thereto or a connector for a hypodermic needle, such as a Luer fitting. The open proximal end of the syringe barrel generally includes an integral radial flange and a stopper is inserted by the pharmaceutical manufacturer following loading of the barrel with a suitable medicament, drug or vaccine. The plunger of a prefilled syringe generally includes a stopper, which is moveable in the syringe barrel, a plunger rod, which extends through the open proximal end of the barrel with a thumb pad is typically integrally formed on the proximal end of the rod. The syringe barrel is typically formed of glass, but may be formed of any suitable material including plastic and metal. The plunger and stopper assembly allows the user to apply manual force to the plunger, driving the stopper through the barrel and causing the medicament, drug or vaccine to be delivered through the needle cannula to the patient during an injection.

The use of any sharp-pointed piercing element entails the risk of an accidental needle stick. To avoid accidental needle sticks, the prior art has proposed various types of safety shields for syringes including prefilled syringes as described above. Such safety shields typically include a tubular shield or needle cover which is located in a retracted position for injection and an extended position following injection enclosing at least the end point of the needle cannula of the syringe and preventing accidental needle sticks. The tubular shield or needle cover of the syringe shield systems proposed by the prior art are typically mounted on a body having a cavity for receipt of a syringe and the syringe is inserted into the body by the pharmaceutical company after filling the syringe with a suitable medicament, drug or vaccine. Alternatively, the shield may be mounted directly on the barrel of the syringe.

There are generally three types of safety shield systems for syringes proposed by the prior art. The first type may be characterized as manual shield systems. That is, the shield or needle cover is manually manipulated by the user to move the needle cover from the retracted position, wherein the needle is exposed for injection or aspiration in the case of reconstitution or vein test, to the extended position, wherein the needle is enclosed. Such manual shield systems typically include some means to prevent the shield from being inadvertently moved to the extended position and prevent the shield from retracting following shielding of the syringe needle cannula, such as detents, interlocking ribs, threads, spiral grooves and the like. The principal disadvantages of manual syringe shield systems are that there is no positive assurance that the user will properly shield the needle cannula following use or that the needle cover is properly locked in the shielded position. In addition, some designs can allow inadvertent activation of the shield.

A second type of shield systems for syringes may be characterized as active shield systems. Active shield systems will typically include an energizer, such as a spring, which biases the shield or needle cover toward the extended position. Generally, the shield is initially retained in the retracted position by ribs, detents or the like and actuated by some action by the user. The principal advantage of active syringe shield systems is that, upon activation by the user, the shield or needle cover will move to enclose the needle cannula and lock the shield. Such active shield systems are generally activated by a button, movement of a component following injection or other release mechanism. That is, the user can generally activate the shield following injection to avoid contact of the shield with the patient's skin prior to disposal. The principal problem with active shield systems for syringes is that again there is generally no positive assurance that the end user will properly shield the needle cannula of the syringe. Further, the shield may be inadvertently or prematurely activated prior to use as discussed further below. The shield may also be inadvertently or prematurely activated particularly during bulk shipping and processing.

The third type of shield systems may be characterized as passive shield systems. Passive shield systems also include an energizer, such as a spring, biasing the shield or needle cover toward the extended position as described above in regard to the active shield systems. However, the shield system is activated automatically generally upon completion of the injection. The primary disadvantages of the passive shield systems proposed by the prior art are that the user cannot select the timing of the actuation of the shield system and the shield or needle cover may be inadvertently or prematurely activated prior to use or completion of the delivery of the fluid in the syringe. That is, the shield can be activated while the needle cannula remains in the patient or the shield may be prematurely activated, particularly during normal manufacturing and assembly procedures and shipping. Shield systems are generally manufactured and assembled by the manufacturer of the shield system. The shield systems are then transported in bulk to a pharmaceutical company and must be handled using automatic feeding equipment, including feed bowls, etc., possibly resulting in inadvertent or premature activation of the shield.

The prior art also includes passive safety shield systems for syringes, wherein the shield system is actuated upon release of the plunger rod resulting in retraction of the syringe into the shield. However, in such shield systems, the syringe is withdrawn into the shield as the plunger rod is released, requiring the user to maintain the plunger against the force of the spring and requiring complete release of the plunger to shield the needle cannula of the syringe. In addition, the shield may contact the patient's skin.

As described below, the passive shield system of this invention reduces the likelihood of premature activation of the shield and permits the end user to select the timing of the activation of the shield. That is, the user can activate or authorize the activation of the shield after removing the needle cannula from the patient, thereby reducing the risk of hitting the patient's skin with the shield or needle cover. Further, the shield or needle cover moves axially relative to the syringe to enclose the needle cannula and lock the shield in the extended position following actuation, requiring only release of the plunger thumb pad.

SUMMARY OF THE INVENTION

As set forth above, the safety shield system of this invention is passive, but avoids the problems associated with the prior art passive shield systems. The shield system of this invention may be utilized with prefilled syringes of the type described above, but may also be used with other types of injection devices. Premature or inadvertent actuation of the shield system is minimized by an interlock system which allows packing, transportation in bulk and high speed feeding systems in bowls, etc. Further, the needle cover or shield is moved to enclose the needle cannula by release of the plunger, thereby giving the user the option of releasing the needle cover only after complete delivery of the fluid in the syringe and removal of the needle cannula from the patient, while assuring shielding of the syringe needle cannula prior to disposal.

The disclosed embodiment of the passive shield system of this invention includes four components, namely a generally tubular body having an open proximal end for receipt of a syringe, a generally tubular shield or needle cover telescopically supported by the body and extendable from a retracted position, wherein the syringe needle cannula is exposed, to an extended position enclosing the needle, a spring biasing the shield toward the extended position, and an annular or ring shaped member which interlocks with the body to prevent premature actuation of the shield or needle cover and which actuates the shield upon release of the plunger following complete delivery of the substance in the syringe. In the disclosed embodiment of the shield system of this invention, the needle cover or shield is telescopically received within the body and moveable axially to shield the needle cannula of the syringe as described. The spring and the ring shaped member are received in the open proximal end of the body such that the spring is biased between the ring shaped member and the shield. Prior to receipt of the syringe, the ring shaped member serves as a locking member preventing premature actuation of the shield. The ring shaped member or locking member includes a leg which forms a mechanical interlock with the body. In the disclosed embodiment, the ring shaped member includes two opposed axially extending legs which, in the preferred embodiment; extend proximally, preferably beyond the open end of the body, for actuation of the shield as described below. In the disclosed embodiment, the legs include opposed V-shaped locking surfaces which form a mechanical interlock with an opposed surface of the body adjacent the open proximal end preventing inadvertent or premature actuation of the shield during bulk shipping and processing as described above. In one disclosed embodiment, the projecting legs of the ring shaped locking member are partially enclosed or surrounded by walls which minimize inadvertent release of the shield by the user. Upon loading of a syringe in the open proximal open end of the shield system, the syringe flange engages the proximal end of the ring shaped member, driving the ring shaped member distally and the legs of the ring shaped member releasing the interlock between the ring shaped member or locking member and the body for actuation of the shield as now described.

In the preferred embodiment of the shield system of this invention, the tubular needle cover or shield includes at least two fingers which extend axially from the proximal end of the needle cover, each having a radial portion which is received on an opposed radial portion or ledge of the generally tubular body and releasably supports the needle cover or shield on the body. The radial portions on the fingers are operatively spaced relatively axially, such that the fingers function independently during actuation of the shield as described below. However, the radial surfaces or ledges on the body may alternatively be spaced axially and the radial portions of the fingers are then spaced axially only if required. One of the fingers is angled or bowed toward the radial support surface of the body, such that the angled or bowed finger is initially supported on the body prior to actuation of the shield. In the disclosed embodiment, the shield includes four fingers, wherein two opposed pairs of fingers are angled or bowed toward the radial support surfaces of the body and the other pair of fingers extend generally axially or are bowed away from the body, providing balanced support for the shield.

Upon receipt of the syringe in the open proximal end of the shield system, the interlock between the body and the ring shaped member is released and the ring shaped member is free to move axially in the body against the force of the spring. The annular or ring shaped member includes a first distal camming surface opposite the finger. In the disclosed embodiment, the shield includes two pairs of fingers opposite the outwardly angled or bowed fingers being referred to hereinafter as the first pair of fingers. When the tubular shield or needle cover is telescopically received within the body, as described above, the first pair of fingers bowed or angled outwardly and the radial portions are spaced distally from the radial portions of the fingers which extend generally axially or are angled inwardly, which are referred to hereinafter as the second pair of fingers. The first pair of fingers therefore initially retains the shield in a first retracted position. The ring shaped member also includes a second camming or biasing surface or surfaces opposite the second pair of fingers of the needle cover.

The shield is thus actuated in stages, as follows. First, as the injection is made, the thumb pad of the plunger assembly of the syringe engages the proximally extending legs of the ring shaped member, driving the ring shaped member distally in the body. The first camming surfaces of the ring shaped member opposite the first pair of fingers then releases the first pair of fingers and the shield moves axially to a second retracted position because the second biasing or camming surfaces of the ring shaped member opposite the second pair of fingers simultaneously biases the second pair of fingers radially outwardly to receive the radial surfaces on the opposed radial surfaces or ledges of the body, releasably retaining the shield in a second retracted position. In the preferred embodiment, the second retracted position is close to or adjacent the first retracted position of the shield. Then, upon completion of the injection and release of the plunger by the user, the spring biases the ring shaped member proximally, releasing the second pair of fingers, and the shield is then driven distally to shield the needle as described. In the preferred embodiment, the body further includes opposed detents adjacent the distal end of the body which receive a radial portion or annular rib of the shield adjacent its proximal end which prevents retraction of the shield following actuation. The shield system of this invention is thus passive in the sense that an additional action by the user is not required to activate the shield. That is, the shield is automatically activated upon release of the plunger. However, the user can also select the timing of the actuation of the shield, for example, by releasing the plunger after removal of the needle cannula from the patient, thereby eliminating engagement of the needle shield against the skin of the patient. Further, upon release of the syringe plunger by the user, the spring drives the shield from its second retracted position to its extended position, enclosing the syringe needle cannula, rather than retracting the syringe into the shield as disclosed in the prior art. Another advantage of the shield system of this invention is that it may be used with conventional syringes without requiring special plungers, thumb pads, etc. A further advantage is that the shield system of this invention may be designed for different sizes of syringes.

As set forth above, the syringe is received in the open proximal end of the shield system. In the disclosed embodiments, the syringe is retained in the body by opposed abutment surfaces adjacent the open proximal end of the body which receive the flange of the syringe therebetween. In one disclosed embodiment, the open proximal end of the body includes inwardly inclined camming surfaces which are engaged by the flange of the syringe. The camming surfaces bias the retainer elements to retain the syringe flange between the opposed abutment surfaces. The proximal end of the body also includes lateral slots defining the opposed distal abutment surfaces. Finally, the proximal end of the body includes axial slots which receive the legs of the ring shaped or locking member.

In another preferred embodiment, the proximal end of the body is generally planar and the body includes generally hook-shaped retainer elements. The abutment surfaces which retain the syringe flange comprise the generally planar open proximal end of the body and the overlying hook-shaped elements. This embodiment includes two pair of spaced ribs on opposed sides of the body which receive the legs of the locking member therebetween each having an inwardly facing proximal hook-shaped end portion which receives and retains the syringe flange and an outwardly facing proximal hook-shaped end portion which receives the locking portion of the ring shaped member. In this disclosed embodiment, the opposed sides of the proximal open end of the body also includes opposed abutment surfaces supported on posts extending from the planar open end of the body which also receive the syringe flange. In this embodiment, the syringe flange is substantially exposed permitting visual inspection of the securement of the syringe in the body.

Other advantages and meritorious features of the shield system of this invention will be more fully understood from the following detailed description of the preferred embodiments, the appended claims and the drawings, a brief description of which follows. As will be understood, the terms proximally and distally are used herein for descriptive purposes only and the term proximally refers to the components or portions of a component closest to the hand of the user, such as a healthcare worker or patient, and the term distally refers to the component or a portion of a component furthest from the hand of the user. Further, the preferred embodiments of the shield system for syringes described below are intended to be exemplary only and do not limit the invention except as set forth in the appended claims.

BRIEF DESCRIPTION OF THE DRAWINGS

FIG. 1 is a side perspective view of one embodiment of the shield system of this invention prior to receipt of a syringe;

FIG. 2 is a side partially cross-sectioned perspective view of the shield system shown in FIG. 1;

FIG. 3 is a partial side view of FIG. 1 illustrating the interlock feature of this invention with a partial view of a syringe shown in phantom;

FIG. 4 is a top view of FIG. 3 in the direction of view arrows 4-4;

FIG. 5 is an exploded view of the shield system shown in FIG. 1 with a conventional syringe prior to receipt of the syringe in the shield system;

FIG. 6 is a partial side view of the proximal end of the shield system with a syringe received in the shield system;

FIG. 7 is an end cross-sectional view of FIG. 6 in the direction of view arrows 7-7;

FIG. 8 is a perspective side view of the syringe and shield system assembly during use of the syringe for an injection;

FIG. 9 is a side perspective view similar to FIG. 8 upon completion of the injection;

FIG. 10 is a side perspective view similar to FIGS. 8 and 9 following completion of the injection and beginning of release of the plunger;

FIG. 11 is a side perspective view of the syringe and shield system following release of the plunger and extension of the needle cover or shield;

FIG. 13 is a top view of the body of the shield system;

FIG. 14 is a top view of the tubular needle cover or shield;

FIG. 15 is a top view of the annular or ring shaped member;

FIG. 16A is a side partial cross-sectional view of the partially assembled components of FIGS. 13 to 15 in the direction of view arrows X-X, also shown in FIG. 1;

FIG. 16B is a partial side cross-sectional view of the partially assembled components of FIGS. 13 to 15 in the direction of view arrows Y-Y, also shown in FIG. 1;

FIG. 17A is a partial side cross-sectional view of the assembled components of FIGS. 13 to 15 in the direction of view arrows Z-Z, also shown in FIG. 1;

FIG. 21 is a top perspective view of an alternative embodiment of the shield system of this invention with a syringe assembled in the shield system;

FIG. 22 is a top perspective view of the body of the alternative embodiment of the shield system shown in FIG. 21;

DETAILED DESCRIPTION OF THE PREFERRED EMBODIMENTS

Figure 12:
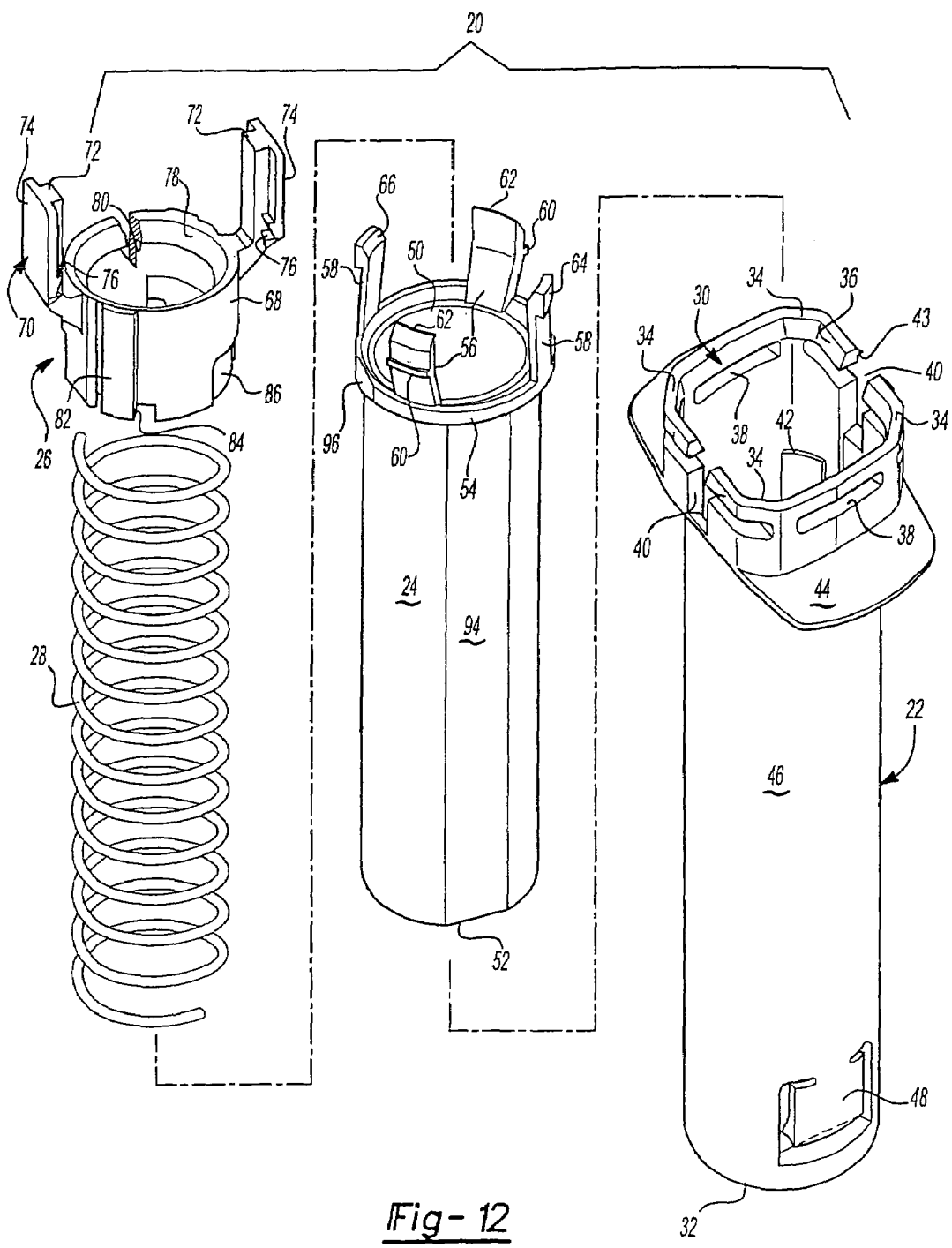
FIG. 12 is an exploded side perspective view of the components of the shield system illustrated in the prior figures.

As set forth above, the preferred embodiments of the shield system 20 shown in FIGS. 1 and 2 includes four components comprising a generally tubular body 22, a generally tubular needle cover or shield 24, an annular or ring shaped member 26 and a spring 28 best shown in the exploded view of FIG. 12. The body 22 includes an open proximal end 30 and an open distal end 32. The open proximal end 30 in the disclosed embodiment is generally rectangular or square having truncated corners 34, inclined internal surfaces 36 at the open proximal end of the body, radial grooves 38 which receive the flange of the syringe described below, axial grooves 40 which extend through the proximal end on opposed sides which receive the legs of the ring shaped member 26 described below, and four radial surfaces or ledges 42 at the truncated corners 34 shown in FIG. 12 which receive the radial portions of the fingers of the needle guard or shield 24 as also described below. The open proximal end 30 of the body 22 may also be elliptical, oval or even cylindrical, but is preferably not cylindrical. The outer edges of the proximal end of the body are hook-shaped having a distal ledge 43 which forms the interlock with the legs of the ring shaped member 26 as discussed below. The body 22 further includes opposed finger flanges 44 adjacent the open proximal end 30, a tubular barrel portion 46 which, in the disclosed embodiment, has a cylindrical outer surface but other shapes may be selected. The tubular barrel portion 46 also includes detents 48 on opposed sides which prevent retraction of the needle cover once extended as also discussed below.

The generally tubular needle cover or shield 24 includes an open proximal end 50 and an open distal end 52 as best shown in FIG. 12. The tubular needle cover or shield 24 further includes an annular external rib 54 adjacent the open proximal end 50 which is received by the detents 48 on the distal end of the body preventing retraction of the shield as described below. The proximal end of the needle cover 24 further includes two pairs of opposed fingers including a first pair of fingers 56 and a second pair of fingers 58. As will be understood from the following description of the operation of the shield system 20 of this invention, the terms first and second pairs of fingers are for descriptive purposes only and the shield system of this invention may include only one finger of each of the pairs of fingers. Each of the pairs of fingers include a radial portion which are able to releasably retain the needle cover 24 in a retracted position, wherein the radial portion 60 of the first pair of fingers 56 is spaced distally from the radial portion 64 of the second pair of fingers 58. The first pair of fingers 56 also include an outwardly inclined camming surface 62 at the proximal ends of the fingers and the second pair of fingers 58 include an inwardly inclined camming surface 66 at their proximal ends.

The ring shaped member 26, also referred to as the locking member because of its function in locking the shield system prior to receipt of the syringe 120 as described below, and shown in FIG. 5, includes an annular body portion 68 and a pair of opposed legs 70 which, in the disclosed embodiment, are generally T-shaped including an inner base portion 72 and an outer bridging portion 74. The bridging portions 74 each include a V-shaped locking portion 76 which interlock with the body portion 22 as described below. The proximal open end of the ring shaped member 26 includes an inclined or frusto-conical surface 78 which tapers inwardly from the proximal open end and an abutment surface 80 at the termination of the inclined surface 78. The body portion 68 of the ring shaped member 26 also includes opposed axial ribs 82 each having an outwardly inclined camming surface 84 at their distal end, best shown in FIG. 16B, and a pair of outwardly biasing surfaces 86 on opposed sides of the body portion 68 having an arcuate distal end surface 88 as shown in FIG. 16A. The coil spring 28 is biased between the abutment surface 80 of the ring shaped member 26 and the inner radial surface 90 between the tubular shield and the first and second pairs of fingers 56 and 58, respectively, as best shown in FIGS. 16A and 16B. The generally cylindrical outer surface of the tubular shield 24 and the radial rib 54 also include flat axially extending surfaces 94 and 96, respectively, which prevent rotation of the shield relative to the body 22 following assembly.

As set forth above, one advantage of the shield system 20 of this invention is that it may be utilized to shield the needle cannula of a conventional syringe, such as a conventional prefilled syringe 120 shown in FIG. 5. As will be understood by those skilled in this art, a conventional prefilled syringe for example generally includes a tubular barrel 122 having an open proximal end 124, a radial finger flange 126 adjacent the open proximal end 124, generally integral with the barrel 122, a needle cannula 128 at the distal end of the barrel 122 and a plunger assembly comprising a stopper 130 moveable within the barrel 122, a plunger rod 132 affixed to the stopper and a thumb pad 134 at the proximal end of the plunger 132, generally formed integral with the rod 132. The needle cannula 128 is generally covered with a needle sheath or cap 136. The barrel 122 may be glass, plastic or metal as set forth above. The stopper 130 is typically formed of an elastomeric material, such as rubber or synthetic rubber, but may also be formed of plastic. The plunger 132 is typically formed of plastic. However, as set forth above, the shield system 20 of this invention may be utilized with any type of injection device and the shield system of this invention is not limited to this type of syringe.

The shield system 20 of this invention may first be assembled by the manufacturer of the shield system prior to receipt of the syringe. The shield system is assembled by inserting the needle cover 24 in the body 22. In the disclosed embodiment, the needle cover or shield 24 is telescopically received in the open proximal end 30 of the body 22, wherein the radial portion 60 of the first pair of fingers 56 is received on the radial inner surfaces 42 of the body as best shown in FIG. 16B. Thus, the radial portion 60 of the first pair of fingers 56 limits axial movement of the tubular shield 24 into the generally tubular body 46. The spring 28 is then inserted into the open proximal end 30 of the body where it is received against the radial surface 90 of the first and second pair of fingers 56 and 58 as shown in FIGS. 16A and 16B. Next, the ring shaped member or locking member 26 is received in the open proximal end 30 of the body, wherein the proximal end of the spring 28 is received against the abutment surface 80 and the spring 28 is thus compressed between the abutment surface 80 of the ring shaped member 26 and the opposed radial surface 90 as shown in FIGS. 16A and 16B. As shown by comparing FIGS. 16A and 16B, the first pair of fingers 56 are angled outwardly or toward the body 22, such that the radial portion 60 is received on the opposed internal radial surface 42 in the normal position. The second pair of fingers 58 extend generally axially from the radial surface 90 or as shown in the disclosed embodiment, the second pair of fingers taper slightly inwardly such that the radial portion 64 of the second pair of fingers 58 will not be received on the opposed radial inner surface 42 of the body unless the fingers are biased outwardly as described below.

The ring shaped member 26 is further compressed against the coil spring 28 until the V-shaped locking portions 76 are received beneath the abutment or hook-shaped outer edge 43 of the body interlocking the shield system as described above. It should also be noted that the base portion 72 of the leg 70 are slidably received in the axial slots 40 of the body as best shown in FIGS. 1 and 2. The inwardly inclined surfaces of the V-shaped locking portion 76 resiliently bias the legs 70 outwardly to receive the transverse surface beneath the locking surface 43 of the body. When the locking or ring shaped member 26 is interlocked with the body as shown in FIGS. 1 and 2, the shield system cannot be inadvertently or prematurely actuated as described above. The shield system can then be transported and processed in bulk, thereby substantially eliminating the problems associated with premature actuation of the shield system during bulk handling and processing and permitting the use of high speed bowl feeders, etc. The shield systems after assembly may then be shipped in bulk to a pharmaceutical company for receipt of a syringe, such as a prefilled syringe containing a drug, vaccine or medicament.

Figures 17B, 18A, 18B, 18C:
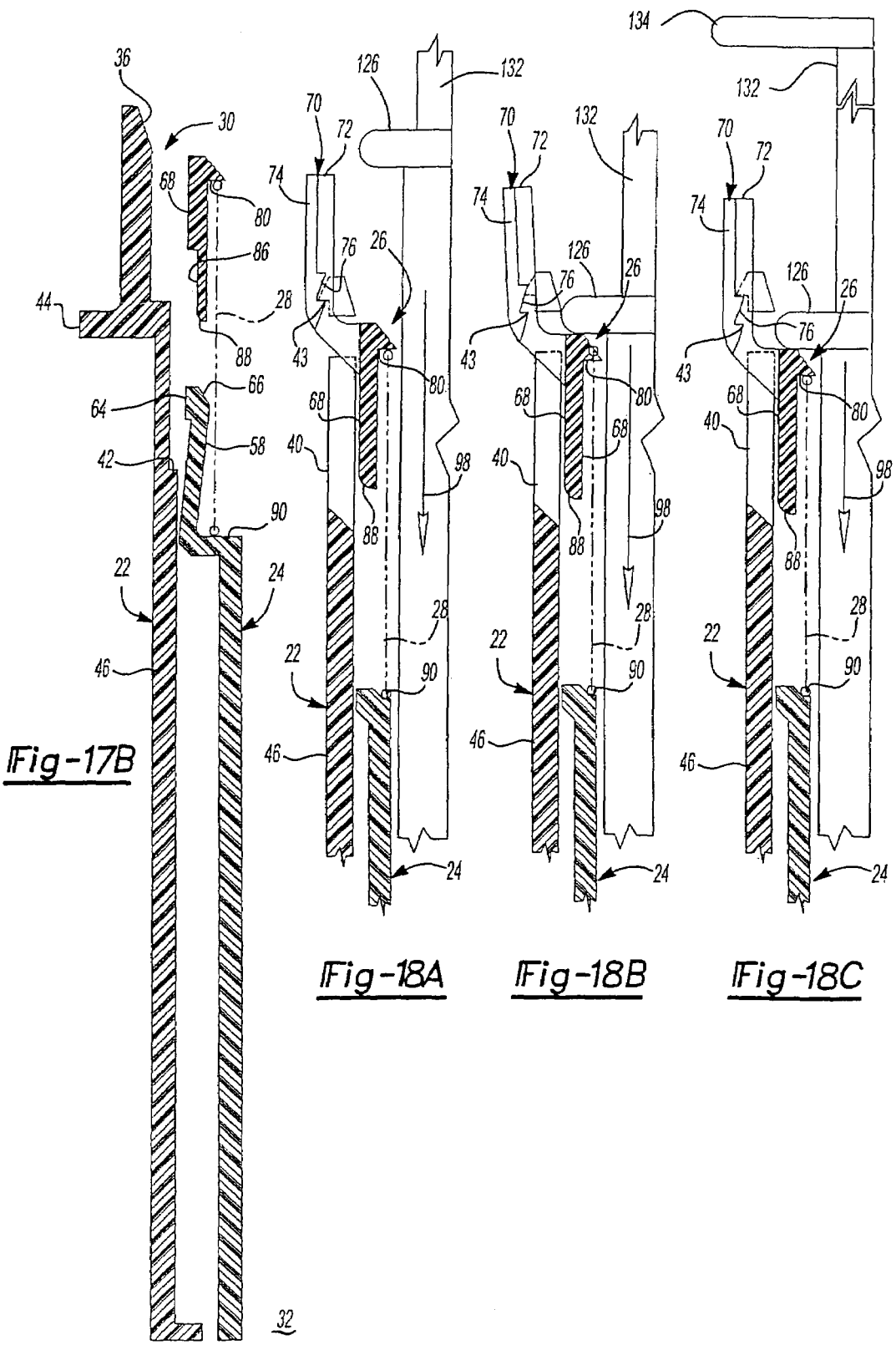
FIG. 17B is a partial cross-sectional view of the assembled components shown in FIG. 17A in the direction of view arrows X-X.
FIGS. 18A to 18C are partial cross-sectional views of the assembled components of FIGS. 13 to 15 in the direction of view arrows Z-Z during assembly of the syringe in the shield system.

The injection device, such as the prefilled syringe 120 shown in FIG. 5, is received in the open proximal end 30 of the body as shown in FIGS. 3 and 5, wherein the sequence of installation of the syringe is shown in FIGS. 18A to 18C as now discussed. As the barrel 122 of the syringe is received in the open proximal end 30 of the shield assembly, as shown by arrow 98, the radial flange 126 at the proximal end of the barrel 122 engages the proximal end of the ring shaped member 26, driving the ring shaped member distally and the V-shaped surfaces 76 then resiliently bias the legs 70 outwardly as shown in FIG. 18B, thereby releasing the interlock between the body and the ring shaped locking member 26 as shown in FIG. 18C, wherein the opposed legs 70 are free to move distally in the slots 40 in the body. As shown in FIG. 18C, however, the legs cannot move proximally (i.e., toward the user) under the force of the coil spring 28 because the proximal ends of the V-shaped portions are received beneath the opposed abutment surface 43 of the body, or the flange is interlocked with the body preventing proximal movement of the ring shaped member. The syringe 120 is now ready for use and actuation of the shield system 20 as shown in FIG. 19A, wherein the radial portion 60 of the first pair of fingers 56 is releasably retained on the opposed radial surface 42 of the body in the retracted position, which is referred to hereinafter as the first retracted position.

The syringe 120 in the shield system 20 may then be used in the normal manner after removal of the cap 136 shown in FIG. 5 and the needle cannula 128 is inserted into the patient, wherein the end user grasps the finger flanges 44 of the body 22 and depresses the thumb pad 134 to make an injection as shown by arrow 100 in FIG. 8. As the thumb pad 134 is depressed to make the injection, it is moved toward the proximal ends of the legs 70 of the ring shaped member 26 as shown in FIGS. 9 and 19B. As set forth above, the legs 70 of the ring shaped member 26 are free to move axially and distally in the slots 40 of the body 22 after release of the interlock between the ring shaped member 26 and the body 22. Continued depression of the thumb pad 134 by the user drives the thumb pad against the proximal ends of the legs 70 and the ring shaped member 26 is thus moved distally as shown in FIG. 19B, wherein the rounded end 88 of biasing surface 86 of the ring shaped member 26 first engages the camming surface 66 and the biasing surface 86 then biases the second pair of legs 58 toward the radial surfaces 42 of the body 22 or, in the disclosed embodiment wherein the shield or needle cover 24 is received within the body 22, radially outwardly, such that the radial portions 64 of the second pair of fingers 58 are coaxially aligned with the internal radial surfaces 42 of the body as shown in FIG. 19B. Continued depression of the thumb pad 134 drives the ring shaped member 26 distally, driving the outwardly inclined camming surfaces 84 against the opposed camming surfaces 62 of the first pair of fingers 56, resiliently biasing the first pair of fingers 56 away from the body 22 or radially inwardly as shown in FIG. 19C, wherein the radial portions 60 are released from the opposed radial surfaces 42 of the body.

Figure 19A:
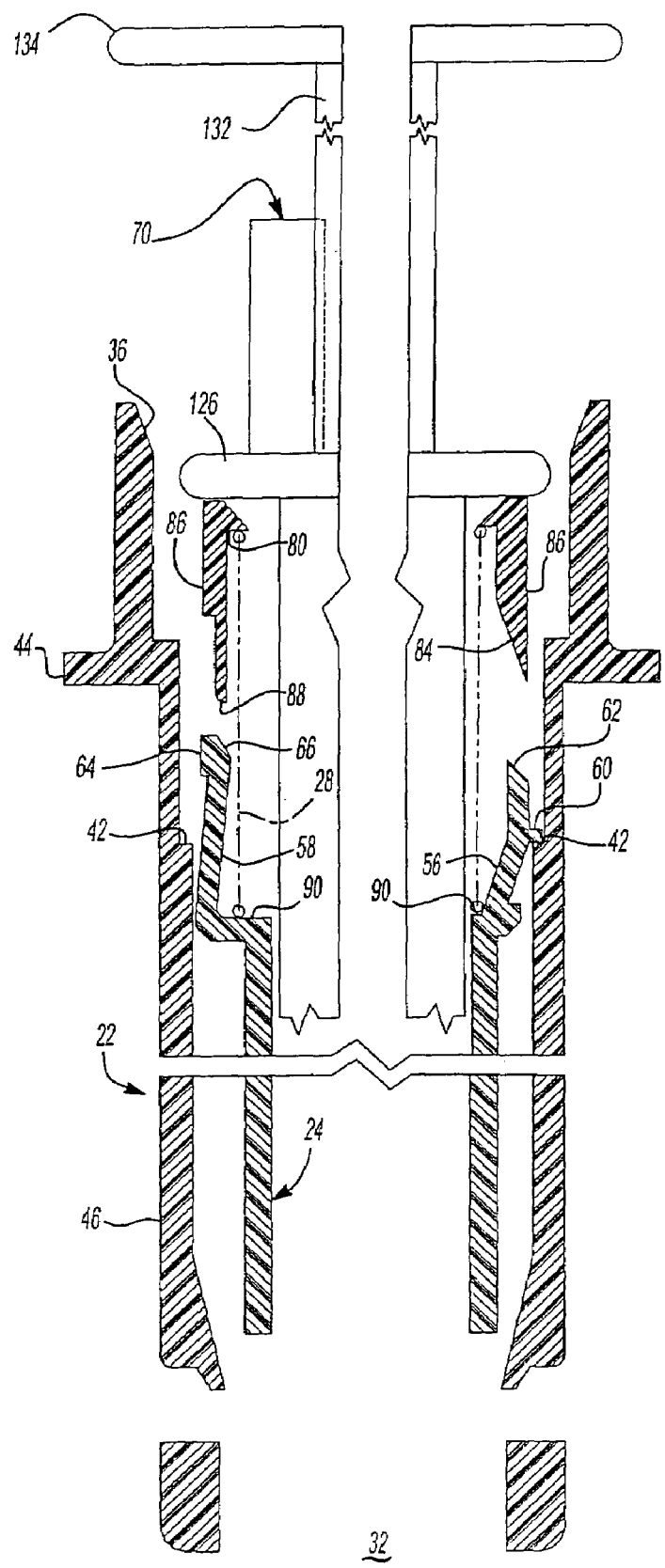
FIGS. 19A to 19E are partial cross-sectional views of the syringe and shield assembly during injection and actuation of the shield, wherein the left-hand portion is a partial cross-section through view arrows X-X and the right-hand portion is a partial cross-section through view arrows Y-Y.
Figure 19B:
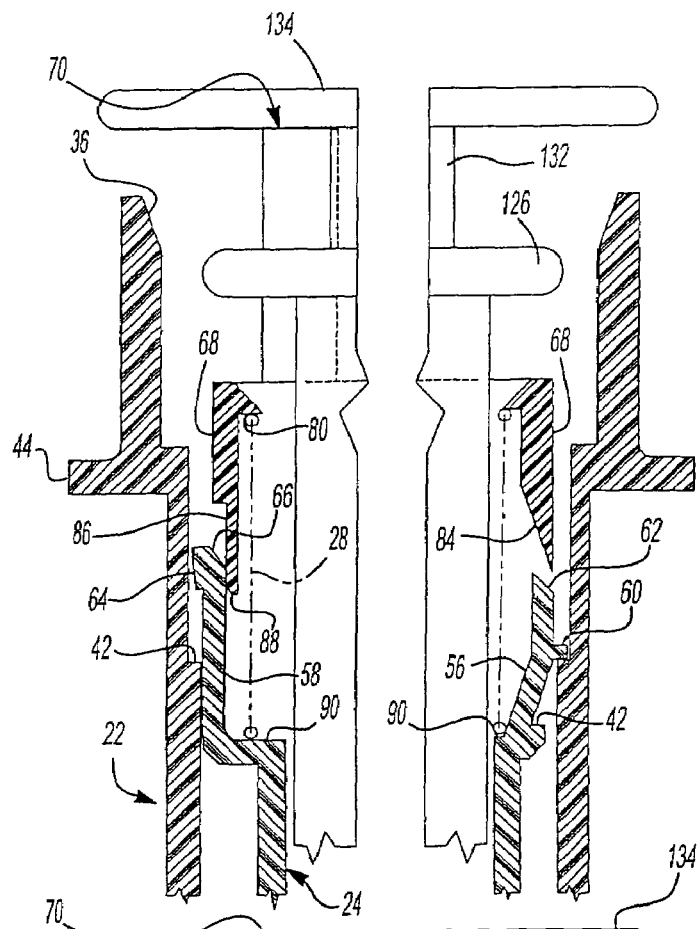
Figure 19C:
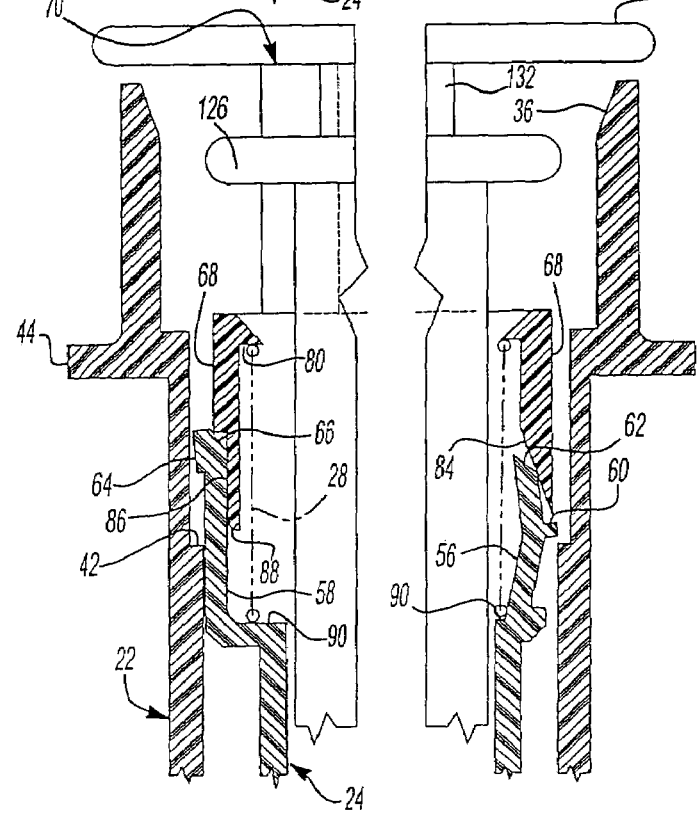
Figure 19D:
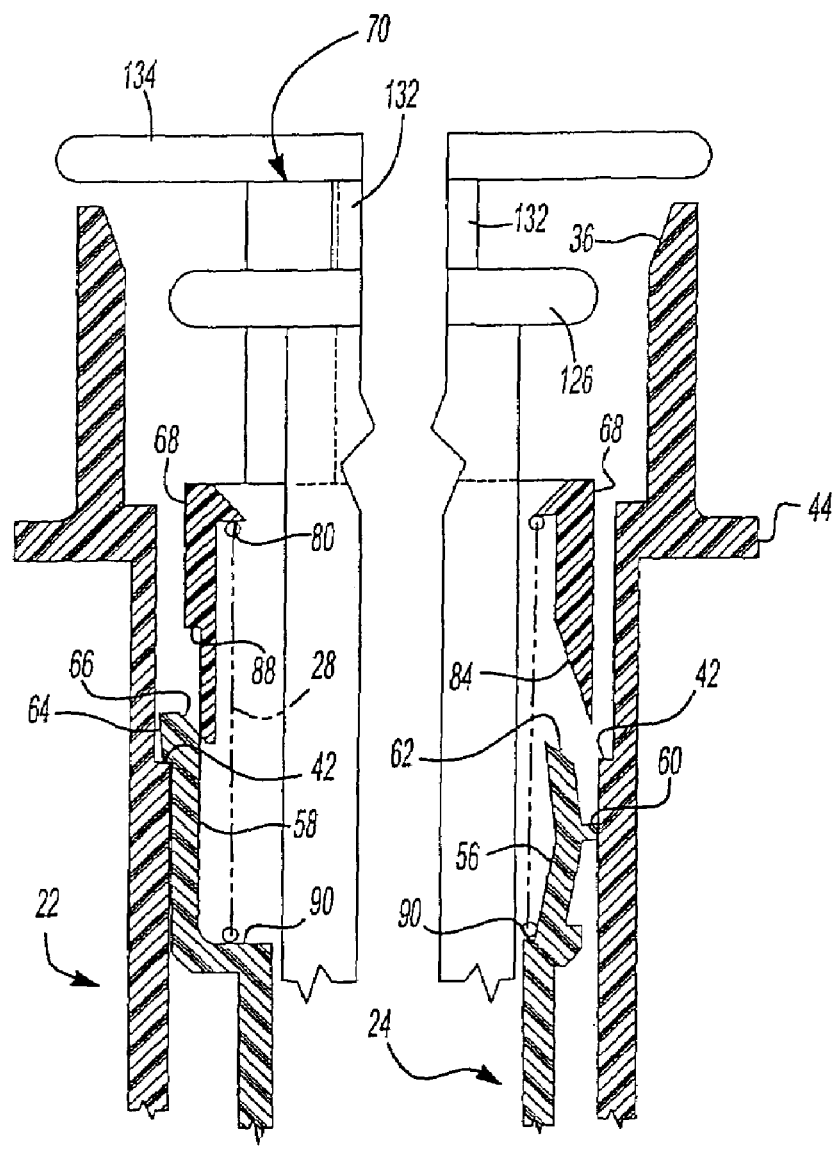

The needle cover or shield 24 then moves distally relative to syringe 120 and body 22 under the force of the spring 28 as shown in FIG. 19D to a second retracted position, wherein the radial portions 64 of the second pair of fingers 58 are received on the opposed radial surfaces 42 of the body and maintained in the second retracted position by the biasing surfaces 86 of the ring shaped member, and the radial portion 60 of the first pair of fingers 56 are spaced distally from the opposed radial surfaces 42 of the body as shown in FIG. 19D. As will then be understood from FIG. 19D, the shield or needle cover 24 is thus releasably retained in the second retracted position as long as the thumb pad 134 of the plunger is maintained by the user.

Figure 19E:
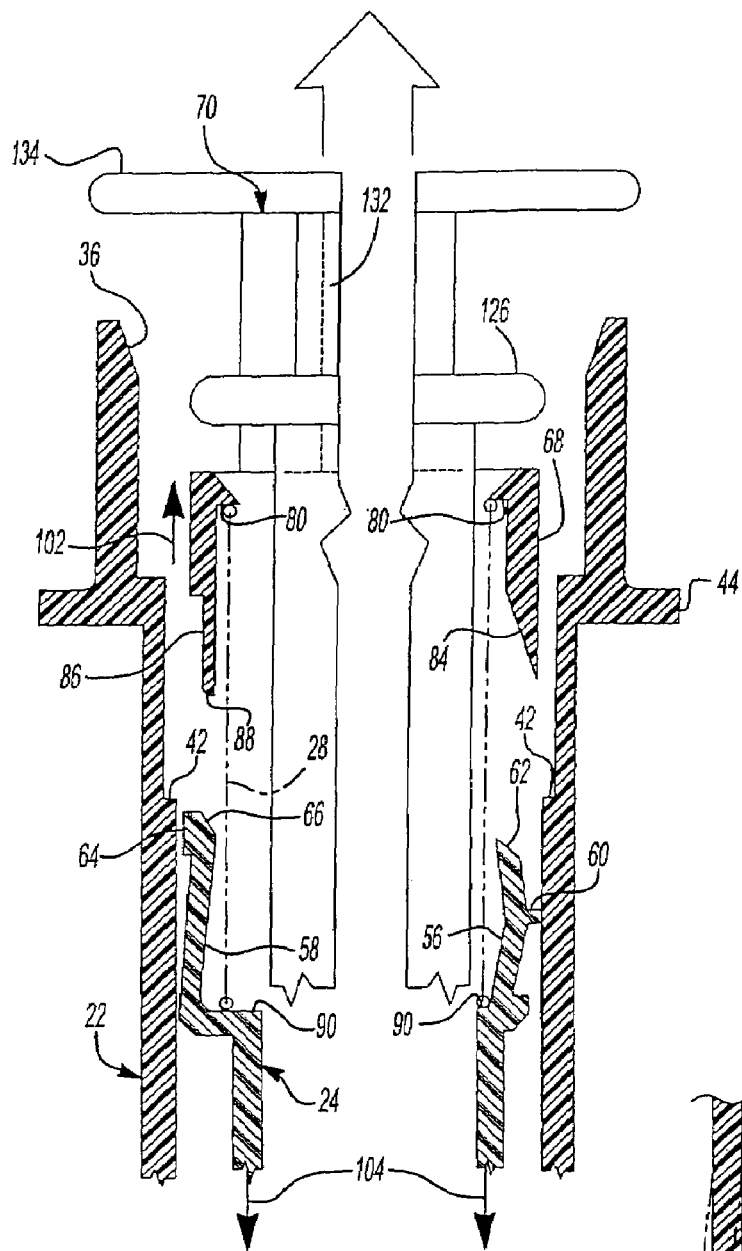
Figure 20:
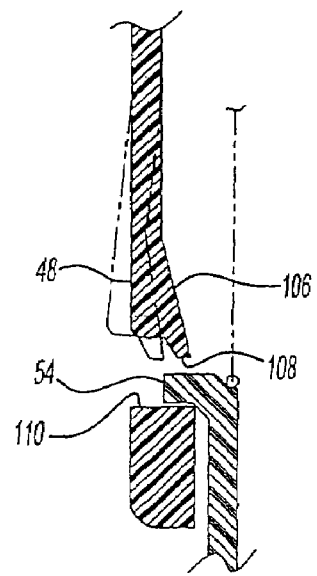
FIG. 20 is a partial cross-sectional side view of the distal end portion of the body and the proximate end portion of the shield illustrating locking of the shield in the extended position.

When the thumb pad 134 is released by the user, the spring 28 drives the ring shaped member 26 proximally as shown by arrow 102 in FIG. 19E, releasing the second pair of fingers 58, such that the second pair of fingers resiliently return to their unbiased position which, in the disclosed embodiment, results in radial inward movement of the second pair of fingers 58, releasing the radial portions 64 of the second pair of fingers from the opposed radial surfaces 42 of the body. The needle cover or shield 24 is then driven distally by the spring 28 as shown by arrows 104 in FIG. 19E and the shield is thus extended from the second retracted position shown in FIG. 19D to the extended position shown in FIG. 11, wherein the needle cover or shield 24 fully encloses the needle cannula 128 of the syringe as shown in FIG. 11. The needle cover 24 is then locked in the extended position by the detents 48 adjacent the distal end of the body 22 as shown in FIG. 20, wherein the radial rib 54 of the needle cover 24 engages the inwardly inclined surface 106, resiliently biasing the detents 48 radially outwardly as shown in phantom in FIG. 20 to receive the radial rib 54 between the opposed abutment surfaces 108 and 110 of the detent 48 of the tubular barrel 46 of the body 22 as shown in FIG. 20. Thus, the needle cover or shield 24 cannot be retracted from the extended position, wherein the needle cannula 128 is enclosed by the needle cover as shown in FIG. 11 to expose the needle cover following injection. The syringe and shield system of this invention may thus be disposed of without potential needle sticks to the persons handling the syringe following injection.

As will now be understood, the user can thus select the timing of the actuation of the needle cover or shield. That is, the user can remove the needle cannula 128 from the patient prior to releasing the thumb pad 134, such that the needle cover 24 does not contact the skin of the patient, which is generally considered undesirable. Alternatively, the user can release the thumb pad following injection while the needle cannula 128 remains in the patient, thereby releasing the needle cover or shield 24.

The embodiment of the shield system 220 illustrated in FIGS. 21 to 25 may be substantially identical to the shield system 20 illustrated in FIGS. 1 to 20 except for the means of retaining the syringe in the body 222. Except for the body 222, the components of the shield system 220 may be identical to the shield system 20 described above and shown in FIGS. 1 to 20, including the needle cover or shield 24, the ring shaped member 26 and the spring 28. Further, the operation of the shield system 220 may be as described above. Thus, only the modified generally tubular body 222 need be described herein in detail for a complete understanding of the shield system 220 shown in FIGS. 21 to 25.

Figure 23:
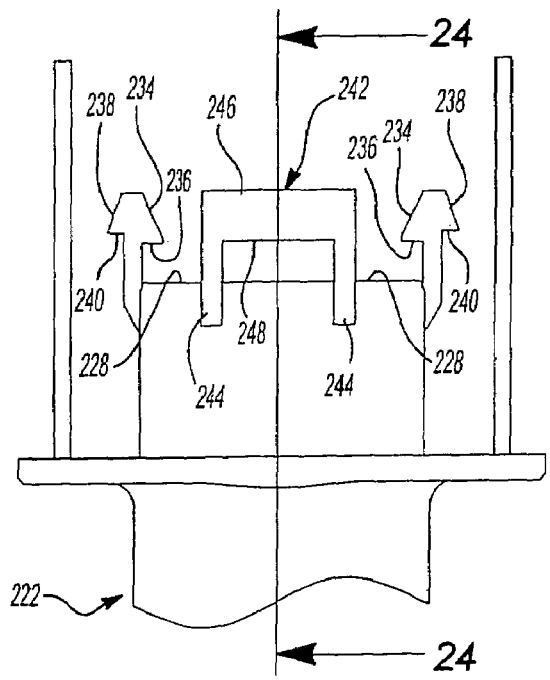
FIG. 23 is a partial side view of the body of the shield system shown in FIG. 22.
Figure 24:
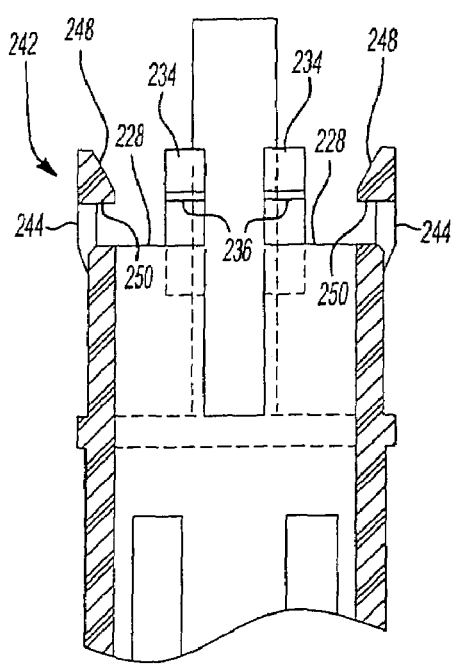
FIG. 24 is a side cross-sectional view of FIG. 23 in the direction of view arrows 24-24.

Referring first to FIGS. 22 to 24, which illustrate the alternative embodiment of the body 222, the generally tubular body 222 includes an open proximal end 224, which receives the barrel 122 of the syringe 120, and an open distal end 226 as described above in regard to FIG. 5. The open proximal end 224 in this embodiment includes a generally rectangular or square planar end wall 228 having truncated corners 230 as described above. However, the shape of the proximal end of the body 222 may be any convenient shape as described above. In this embodiment, the proximal end of the body 222 includes a plurality of generally hook-shaped retainer elements which project proximally from the planar end wall 228 which retain the syringe 120 in the body 222 as now described.

The retainer elements include two pair of opposed spaced integral axial ribs 232 which project proximally from the planar end wall 228 on opposed sides of the end wall each having an inclined inner surface 234 terminating in an undercut 236 and an inclined outer surface 238 terminating in an undercut 240. As described below, the spaced axial ribs 232 receive the axially projecting legs 70 of the ring shaped element 26 therebetween as shown in FIG. 21. The retainer elements 242 on the opposed sides of the proximal end of the body each include axially projecting posts 244, which are integrally formed with the side walls, and a bridging portion 246 each having an inclined camming surface 248 and an undercut 250. As shown in FIGS. 23 and 24, the undercuts 236 and 248 are aligned axially and form proximal abutment surfaces with the opposed planar end wall 228. Thus, as described above, the syringe 120 is received in the open proximal end 224 of the body 222 as shown in FIG. 5, wherein the flange 126 of the barrel 120 of the syringe is received against the inwardly inclined camming surfaces 234 and 248, resiliently biasing the retainer elements outwardly and receiving the flange 126 of the syringe between the opposed abutment surfaces 236 and 250 of the retainer elements and the opposed planar end wall 228 of the body, retaining the syringe 120 in the body. One advantage of this means of retaining the syringe in the body is that the flange 126 of the syringe is exposed, permitting inspection of the retainer elements following assembly to confirm that the syringe is securely retained in the body following assembly.

Figure 25:
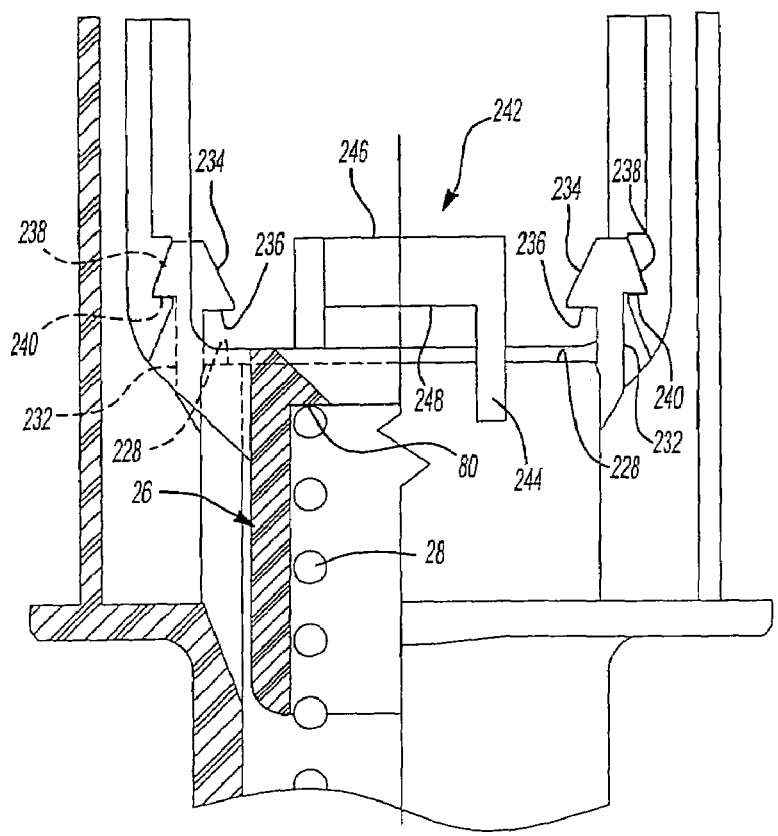
FIG. 25 is a side partially cross-sectioned view of the shield system illustrated in FIG. 21 prior to receipt of the syringe.

As described above in the regard to the assembly of the shield system 20, the needle cover or shield 24 (not shown in FIGS. 21 to 25) but described above, is first received in the body, the spring 28 is then received in the body and the ring shaped member or locking member 26 is then received in the body and biased against the spring, wherein the proximally extending legs 70 are received between the ribs 232 and the V-shaped locking portions 76 interlock with the outer inclined surfaces 238 and the undercut 240 as shown in FIG. 25. Thus, the assembly of the shield system 220 is substantially identical to the assembly of the shield system 20 described above, wherein the locking member 26 forms an interlock with the proximal end of the body prior to receipt of the syringe 120 limiting premature or inadvertent actuation of the shield system.

This embodiment of the shield system 220 includes a further optional security feature reducing the likelihood of premature or inadvertent actuation of the shield system either during bulk shipping and handling or by the user. This embodiment includes protective walls 252 on opposed sides of the ribs 232 which receive the projecting legs 70 of the ring shaped member 26 as shown in FIG. 21. The protective walls 252 preferably have an axially length greater than the length of the projecting legs 70, thereby reducing the likelihood of inadvertent contact with the legs 70 during shipping and handling and by the user. As described above, the shield systems 20 and 220 are actuated by depressing the thumb pad 134, which then engages the projecting legs 70 of the ring shaped member 26, thereby moving the ring shaped member 26 distally. Then upon release of the thumb pad 134, the needle cover 24 shown in the prior figures is released and the spring 28 then drives the shield to the extended position shown in FIG. 11. The walls 252 are spaced from the ribs 232 sufficient to accommodate the receipt of the thumb pad 134 between the walls 252, but reduce the likelihood of inadvertent engagement of the legs 70 either during bulk shipping and processing or by the user.

In the disclosed embodiment, the protective walls 252 are planar and integrally formed with the finger grip 254 of the body. However, the walls can be arcuate, for example, to partially surround the legs 70 and the walls can also be formed integral with the proximal end of the body distally below the ribs 232. As described above, the shield is preferably locked in the extended position following actuation and the disclosed embodiment of the body 222 includes detents 256 which lock the shield in the extended position as described above. As set forth above, except for body 222, the remaining components of the shield system 220 may otherwise be identical to the components of the shield system 20, including the needle cover or shield 24, the spring 28 and the ring shaped member 26.

Based upon the above description of the preferred embodiments of the shield system for a syringe of this invention, the assembly of the shield system and method of operation, the method of assembling a shield system 20 or 220 on a syringe, such as the syringe 120 disclosed, comprises assembling the shield system 20 or 220 including the generally tubular body 22 or 222, the generally tubular needle cover or shield 24, the spring 28, and the locking member 26 which, in the disclosed embodiment is annular or ring shaped, wherein the shield 24 is in a retracted position and the locking member is interlocked with the body, preventing inadvertent or premature release of the shield from the retracted position to the extended position prior to receipt of the syringe in the shield system 20 or 220. The method then includes inserting a syringe 120 in the shield system 20 or 220 through the open proximal end 30 or 224 of the body, thereby releasing the locking member from the body and permitting actuation of the shield as described above. As also described above, the method of shielding a needle cannula of a syringe of this invention includes injecting a fluid through the needle cannula by driving the plunger 132 and stopper 130 through the barrel 122 of the syringe, then releasing the plunger, thereby releasing the needle cover or shield 24 from a retracted position to an extended position enclosing the needle cannula.

The components of the shield systems 20 and 220 of this invention may be formed of various materials. For example, the body 22, or 222, needle cover 24 and the ring shaped member 26 may be formed of plastic including clear plastic for visualization of the content of the syringe 120. The body 22 or 222 and needle cover 24 are preferably formed of a resilient or semi-rigid plastic for operation of the interlock and release of the shield as described above. As will be understood by those skilled in this art, various modifications may be made to the shield systems 20 and 220 of this invention within the purview of the appended claims. For example, features of the shield system of this invention can be incorporated in a shield system wherein the shield is telescopically received around the exterior surface of the body, particularly including the interlock feature. Further, the ring shaped member or locking member 26 may include only one leg 70 or a plurality of legs greater than two. Although the locking member 26 is preferably ring shaped or annular as disclosed, other shapes may also be utilized. Further, as described above, the fingers 56 and 58 of the needle cover 24 are preferably opposed pairs of fingers as disclosed providing balanced support of the shield, the shield system of this invention may include only two fingers or a plurality of fingers greater than two. Finally, the internal radial support surfaces 42 in the body, which releasably support the needle cover in the body, may be spaced axially for each of the pairs of fingers, wherein the radial portions would be adjusted axially accordingly. Having described the preferred embodiments of the passive safety shield system for syringes of this invention and method of assembly and operation, the invention is now claimed as follows.

The invention claimed is:

1. A method of assembling a shield system on a syringe, said syringe including a tubular barrel, a needle cannula extending from a distal end of said barrel and a stopper in said barrel, said shield system including a generally tubular body having an open proximal end, a generally tubular shield telescopically supported by said body and moveable relative to said body from a first retracted position to a second retracted position, and from the second retracted position to an extended position, a locking member and a spring biasing said shield toward said extended position, said method comprising:

assembling said shield system including said body, shield, spring and locking member, with said shield in said first retracted position and interlocking said locking member with said body, thereby preventing inadvertent release of said shield to said extended position prior to receipt of said syringe in said shield system; and inserting said syringe in said shield system through said open proximal end of said body, thereby releasing said locking member from said body and permitting actuation of said shield system and extension of said shield to said extended position enclosing said needle cannula, whereby, activation of a plunger rod of the syringe causes movement of said locking member to cause said shield to move from said first retracted position to said second retracted position, and release of the plunger causes movement of said locking member to cause said shield to move from said second retracted position to said extended position.

2. The method of assembling a shield system on a syringe as defined in claim 1, wherein said locking member is a separate ring shaped element having at least one axially extending leg portion, said method including mechanically interlocking said leg portion to said body of said shield system.

3. The method of assembling a shield system on a syringe as defined in claim 2, wherein said barrel of said syringe includes a radial flange portion adjacent an open proximal end of said barrel and said method includes inserting said syringe into said open proximal end of said body and said radial flange portion of said barrel engaging and releasing said leg of said locking member from said body.

4. The method of assembling a shield system on a syringe as defined in claim 1, wherein said shield includes a finger having a radial portion releasably engaging a radial surface of said body retaining said shield in said second retracted position relative to said body, and said method further including driving said locking member against said finger, thereby releasing said finger, and said spring then driving said shield from said second retracted position to said extended position enclosing said needle cannula of said syringe.

5. The method of assembling a shield system on a syringe as defined in claim 4, wherein the plunger rod has a thumb pad at a proximal end of the plunger rod, said method including driving said thumb pad against a proximal end of said locking member, thereby driving a distal end of said locking member against said finger of said shield.

6. The method of assembling a shield system on a syringe as defined in claim 1, wherein said method includes mechanically interlocking said locking member with said body of said shield system, and said barrel of said syringe includes a radial flange adjacent an open proximal end of said barrel, including inserting said syringe in said open proximal end of said body and said radial flange of said barrel then releasing said mechanical interlock of said locking member with said body.

7. The method of assembling a shield system on a syringe as defined in claim 1, said method further including injecting a fluid through said needle cannula by driving said plunger rod and said stopper through said barrel, then releasing said plunger rod, thereby releasing said shield from said second retracted position, said spring then driving said shield to said extended position enclosing said needle cannula of said syringe.

\* \* \* \* \*